US006979562B2

(12) United States Patent
Cheung

(10) Patent No.: US 6,979,562 B2
(45) Date of Patent: *Dec. 27, 2005

(54) METHODS AND COMPOSITIONS FOR TREATING GASTROPARESIS

(75) Inventor: Ling Yuk Cheung, New Territories (HK)

(73) Assignee: Ultra Biotech Limited, Douglas (GB)

( * ) Notice: Subject to any disclaimer, the term of this patent is extended or adjusted under 35 U.S.C. 154(b) by 20 days.

This patent is subject to a terminal disclaimer.

(21) Appl. No.: 10/717,132

(22) Filed: Nov. 18, 2003

(65) Prior Publication Data

US 2005/0106167 A1 May 19, 2005

(51) Int. Cl.⁷ .............................. C12N 1/14; C12N 13/00
(52) U.S. Cl. ................................ 435/173.1; 435/255.1; 435/255.2; 435/173.8
(58) Field of Search ................... 424/195.16; 435/173.1, 435/173.8, 255.1, 255.2

(56) References Cited

U.S. PATENT DOCUMENTS

| | | |
|---|---|---|
| 2,107,830 A | 2/1938 | Liebesny et al. |
| 3,150,979 A | 9/1964 | Ensley |
| 3,711,392 A | 1/1973 | Metzger |
| 3,870,599 A | 3/1975 | Azarowicz |
| 3,923,279 A | 12/1975 | Gresley et al. |
| 3,939,279 A | 2/1976 | Kawano et al. |
| 3,968,254 A | 7/1976 | Rhodes et al. |
| 3,997,675 A | 12/1976 | Eichelburg |
| 4,041,182 A | 8/1977 | Erickson et al. |
| 4,081,367 A | 3/1978 | Hulls et al. ................. 210/610 |
| 4,118,512 A | 10/1978 | Eichelburg |
| 4,183,807 A | 1/1980 | Yoshizawa et al. ......... 210/611 |
| 4,211,645 A | 7/1980 | Zajic et al. ................. 210/611 |
| 4,348,483 A | 9/1982 | Skogerson |
| 4,559,305 A | 12/1985 | Zajic et al. ................. 435/243 |
| 4,816,158 A | 3/1989 | Shimura et al. ............ 210/610 |
| 5,047,250 A | 9/1991 | Prieels et al. |
| 5,075,008 A | 12/1991 | Chigusa et al. ............. 210/610 |
| 5,082,662 A | 1/1992 | Laurent et al. |
| 5,082,936 A | 1/1992 | Jamas et al. |
| 5,106,594 A | 4/1992 | Held et al. .................. 422/292 |
| 5,158,788 A | 10/1992 | Lavens et al. |
| 5,416,010 A | 5/1995 | Langenberg et al. ........ 435/468 |
| 5,476,787 A | 12/1995 | Yokoyama et al. ...... 435/262.5 |
| 5,504,079 A | 4/1996 | Jamas et al. |
| 5,567,314 A | 10/1996 | Chigusa et al. ............. 210/150 |
| 5,578,486 A | 11/1996 | Zhang ........................ 435/243 |
| 5,665,352 A | 9/1997 | Blehaut et al. |
| 5,707,524 A | 1/1998 | Potter ......................... 210/606 |
| 5,866,116 A | 2/1999 | Yaegaki |
| 5,879,928 A | 3/1999 | Dale et al. .................. 435/264 |
| 5,952,020 A | 9/1999 | Lizak |
| 5,981,219 A | 11/1999 | Flugge et al. |
| 6,036,854 A | 3/2000 | Potter ......................... 210/177 |
| 6,045,834 A | 4/2000 | Howes et al. |
| 6,143,731 A | 11/2000 | Jamas et al. |
| 6,159,510 A | 12/2000 | Lizak |
| 6,197,295 B1 | 3/2001 | Hsia et al. |
| 6,214,337 B1 | 4/2001 | Hayen et al. |
| 6,391,617 B1 | 5/2002 | Cheung ....................... 435/254 |
| 6,391,618 B1 | 5/2002 | Cheung ....................... 435/255 |
| 6,391,619 B1 | 5/2002 | Cheung ....................... 435/255 |
| 6,416,982 B1 | 7/2002 | Zhang |
| 6,416,983 B1 | 7/2002 | Cheung |
| 6,436,695 B1 | 8/2002 | Cheung ....................... 435/254 |

(Continued)

FOREIGN PATENT DOCUMENTS

| | | |
|---|---|---|
| CN | 1110317 A | 10/1995 |
| CN | 1207873 | 2/1999 |
| CN | 1309175 | 8/2001 |
| EP | 0041373 | 12/1981 |
| EP | 553377 | 8/1993 |
| EP | 1375652 | 1/2004 |
| ES | 475500 | 4/1979 |
| FR | 2222433 | 10/1974 |
| GB | 1397873 | 6/1975 |
| JP | 60028893 | 2/1985 |
| RU | 415983 A | 11/1974 |
| RU | 1071637 | 2/1984 |
| SU | 1722364 | 3/1992 |
| SU | 1750570 | 7/1992 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/62981 | 8/2002 |
| WO | WO 02/62982 | 8/2002 |
| WO | WO 02/62983 | 8/2002 |
| WO | WO 02/62984 | 8/2002 |
| WO | WO 02/62985 | 8/2002 |
| WO | WO02070436 | 9/2002 |
| WO | WO 02/070682 A2 | 9/2002 |
| WO | WO02070683 | 9/2002 |
| WO | WO2004108919 | 12/2004 |

OTHER PUBLICATIONS

Agarwal N. et al., "Selection of Saccharomyces cerevisiae strains for use as a microbial feed additive," *Letters in Applied Microbiology*, 31:270–273 (2000).

Asami, K. et al., "Real–Time Monitoring of Yeast Cell Division by Dielectric Spectroscopy", *Biophysical Journal*, 76, pp. 3345–3348 (1999).

(Continued)

*Primary Examiner*—Bruce R. Campell
*Assistant Examiner*—Randall Winston
(74) *Attorney, Agent, or Firm*—Fish & Neave IP Group Ropes & Gray LLP; James F. Haley, Jr.; Z. Ying Li

(57) ABSTRACT

Compositions comprising a plurality of yeast cells, wherein said plurality of yeast cells are characterized by their ability to treat gastroparesis in a subject (e.g., stimulating stomach contraction, reducing abnormal gastric acid and/or pepsin production), as a result of having been cultured in the presence of an alternating electric field having a specific frequency and a specific field strength. Also included are methods of making and using such compositions.

12 Claims, 3 Drawing Sheets

U.S. PATENT DOCUMENTS

| | | |
|---|---|---|
| 6,440,713 B1 | 8/2002 | Cheung ..................... 435/173 |
| 6,596,272 B2 | 7/2003 | Cheung |
| 6,596,273 B2 | 7/2003 | Cheung |
| 6,649,383 B1 | 11/2003 | Cheung ................... 435/173.1 |
| 6,660,508 B1 | 12/2003 | Cheung ................... 435/173.1 |
| 6,699,496 B1 | 3/2004 | Kojima et al. |
| 6,761,886 B2 | 7/2004 | Cheung |
| 6,800,466 B2 | 10/2004 | Cheung |
| 6,828,131 B2 | 12/2004 | Zhang |
| 6,828,132 B2 | 12/2004 | Cheung |
| 2002/0099026 A1 | 7/2002 | Goodman et al. |
| 2002/0123127 A1 | 9/2002 | Cheung ..................... 435/254 |
| 2002/0123129 A1 | 9/2002 | Cheung ..................... 435/254 |
| 2002/0123130 A1 | 9/2002 | Cheung ..................... 435/262 |
| 2003/0230126 A1 | 12/2003 | Cheung |
| 2003/0230245 A1 | 12/2003 | Cheung |
| 2003/0232038 A1 | 12/2003 | Cheung |
| 2003/0232039 A1 | 12/2003 | Cheung |
| 2003/0232059 A1 | 12/2003 | Cheung |
| 2003/0235565 A1 | 12/2003 | Cheung |
| 2003/0235566 A1 | 12/2003 | Cheung |
| 2003/0235567 A1 | 12/2003 | Cheung |
| 2003/0235568 A1 | 12/2003 | Cheung |
| 2003/0235569 A1 | 12/2003 | Cheung |
| 2003/0235570 A1 | 12/2003 | Cheung |
| 2004/0001812 A1 | 1/2004 | Cheung |
| 2004/0001813 A1 | 1/2004 | Cheung |
| 2004/0001814 A1 | 1/2004 | Cheung |
| 2004/0001815 A1 | 1/2004 | Cheung ................... 424/93.51 |
| 2004/0001857 A1 | 1/2004 | Cheung ................. 424/195.16 |
| 2004/0001858 A1 | 1/2004 | Cheung ................. 424/195.16 |
| 2004/0001859 A1 | 1/2004 | Cheung ................. 424/195.16 |
| 2004/0001860 A1 | 1/2004 | Cheung ................. 424/195.16 |
| 2004/0001861 A1 | 1/2004 | Cheung ................. 424/195.16 |
| 2004/0005335 A1 | 1/2004 | Cheung |
| 2004/0005337 A1 | 1/2004 | Cheung ................. 424/195.16 |
| 2004/0005680 A1 | 1/2004 | Cheung |
| 2004/0168492 A1 | 9/2004 | Cheung |
| 2004/0252492 A1 | 12/2004 | Cheung |
| 2004/0253251 A1 | 12/2004 | Cheung |
| 2004/0253252 A1 | 12/2004 | Cheung |
| 2004/0253253 A1 | 12/2004 | Cheung |
| 2004/0253254 A1 | 12/2004 | Cheung |
| 2004/0253255 A1 | 12/2004 | Cheung |
| 2004/0253256 A1 | 12/2004 | Cheung |
| 2004/0253257 A1 | 12/2004 | Cheung |
| 2004/0253258 A1 | 12/2004 | Cheung |
| 2004/0253259 A1 | 12/2004 | Cheung |
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0253268 A1 | 12/2004 | Cheung |
| 2004/0265990 A1 | 12/2004 | Cheung |

OTHER PUBLICATIONS

Balcer–Kubiczek, E.K. et al., "Expression Analysis of Human HL60 Cells Exposed to 60 Hz Square–or Sine–Wave Magnetic Fields", *Radiation Research*, 153, pp. 670–678 (2000).

Bassett, C.A.L. et al., "Beneficial Effects of Electromagnetic Fields", *Journal of Cellular Biochemistry*, 51, pp. 387–393 (1993).

Binninger, D. M. et al., "Effects of 60Hz AC magnetic fields on gene expression following exposure over multiple cell generations using Saccharomyces cerevisiae", *Bioelectrochemistry and Bioenergetics*, 43(1):83–89 (1997).

Conti, P. et al., "Effect of Electromagnetic Fields on Several CD Markers and Transcription and Expression of CD4", *Immunobiology*, 201, pp. 36–48 (1999).

Deguchi, T. et al., "Nylon biodegradation by lignin–degrading fungi", *Applied and Environmental Microbiology*, 63(1):329–331 (1997).

Dufresne C. et al., "Tea, Kombucha, and Health: A review," *Food Research International*, 33:409–421 (2000).

Gonzalez, A.M. et al., "Effects of an Electric Field of Sinusoidal Waves on the Amino Acid Biosynthesis by Azotobacter", *Z. Naturforsch*, 35, pp. 258–261 (1980).

Goodman, E.M. et al., "Effects of Electromagnetic Fields on Molecules and Cells", *International Review of Cytology*, 158, pp. 279–339 (1995).

Greenwalt C.J. et al., "Kombucha, the fermented tea: Microbiology, composition, and claimed health effects," *Journal of Food Protection*, 63:976–981 (2000).

Grospietsch, T. et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

Grundler W. et al., "Resonant–like dependence at yeast growth rate on microwave frequencies," *The British Journal of Cancer*, Supplement, England Mar. 1982, 45:206–208 (1982).

Grundler, W. et al., "Mechanisms of Electromagnetic Interaction with Cellular Systems", *Naturwissenschaften*, 79, pp. 551–559 (1992).

Grundler, W. et al., "Nonthermal Effects of Millimeter Microwaves on Yeast Growth", *Z. Naturforsch*, 33, pp. 15–22 (1978).

Ivaschuk, O.I. et al., "Exposure of Nerve Growth Factor–Treated PC12 Rat Pheochromocytoma Cells to a Modulated Radiofrequency Field at 836.55 MHz: Effects on c–*jun* and c–*fos* Expression", *Bioelectromagnetics*, 18, pp. 223–229 (1997).

Jelinek, F. et al., "Microelectronic Sensors for Measurement of Electromagnetic Fields of Living Cells and Experimental Results", *Bioelectrochemistry and Bioenergetics*, 48, pp. 261–266 (1999).

Lacy–Hulbert, A. et al., "Biological Responses to Electromagnetic Fields", *FASEB Journal*, 12, pp. 395–420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

Lin, H. et al., "Magnetic Field Activation of Protein–DNA Binding", *Journal of Cellular Biochemistry*, 70, pp. 297–303 (1998).

Lin, H. et al., "Specific Region of the c–*myc* Promoter Is Responsive to Electric and Magnetic Fields", *Journal of Cellular Biochemistry*, 54, pp. 281–288 (1994).

Liu C.H. et al., "The Isolation and identification of microbes from a fermented tea beverage, Haipao, and their interactions during Haipao fermentation," *Food Microbiology* (London), 13:407–415 (1996).

Loberg, L.I. et al., "Expression of Cancer–Related Genes in Human Cells Exposed to 60 Hz Magnetic Fields", *Radiation Research*, 153, pp. 679–684 (2000).

Mayser P. et al., "The yeast spectrum of the 'tea fungus Kombucha'," *Mycoses*, Blackwell, Berlin, Germany, 38:289–295 (1995).

Moore, R.L., "Biological Effects of Magnetic Fields: Studies with Microorganisms", *Canadian Journal of Microbiology*, 25, pp. 1145–1151 (1979).

Morehouse, C.A. et al., "Exposure of Daudi Cells of Low–Frequency Magnetic Fields Does Not Elevate MYC Steady–State mRNA Levels", *Radiation Research*, 153, pp. 663–669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

Novelli, G. et al., "Study of the Effects of DNA of Electromagnetic Fields Using Clamped Homogeneous Electric Field Gel Electrophoresis", *Biomedicine & Pharmacotherapy*, 45, pp. 451–454 (1991).

Phillips, J.L., "Effects of Electromagnetic Field Exposure on Gene Transcription", *Journal of Cellular Biochemistry*, 51, pp. 381–386 (1993).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material–relation to food processing", *Radiation Physics and Chemistry*, 45(4): 591–607 (1995).

Romano–Spica, V. et al., "Ets1 Oncogene Induction by ELF–Modulated 50 MHz Radiofrequency Electromagnetic Field", *Bioelectromagnetics*, 21, pp. 8–18 (2000).

Surawicz Christina M. et al., "The search for a better treatment for recurrent Clostridium difficile disease: Use of high–dose vancomycin combined with Saccharomyces boulardii," *Clinical Infectious Diseases*, 31:1012–1017 (2000).

Trosko, J.E., "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

Van den Bogaerde J. et al., "Immune sensitization to food, yeast and bacteria in Crohn's disease," *Alimentary Pharmacology & Therapeutics*, 15:1647–1653 (2001).

Van Rensburg, P. et al., "Engineering yeast for efficient cellulose degradation", *Yeast*, 14(1):67–76 (1998).

Ventura, C. et al., "Elf–pulsed Magnetic Fields Modulate Opioid Peptide Gene Expression in Myocardial Cells", *Cardiovascular Research*, 45, pp. 1054–1064 (2000).

Woodward, A.M. et al., "Genetic Programming as an Analytical Tool for Non–linear Dielectric Spectroscopy", *Bioelectrochemistry and Bioenergetics*, 48, pp. 389–396 (1999).

Yonetani, T. et al., "Electromagnetic Properties of Hemoproteins", *The Journal of Biological Chemistry*, 247, pp. 2447–2455 (1972).

Zhang, L. et al., "Electrostimulation of the Dehydrogenase System of Yeast by Alternating Currents", *Bioelectrochemistry and Bioenergetics*, 28, pp. 341–353 (1992).

"Saccharomyces cerevisiae Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

Born et al., "The Saccharomyces Boulardii Therapy of HIV–Associated Diarrhea", *Deutsche Medizinische Wochenschrift*, 118(20):765 (1993). (in German with English translation).

Dutta et al., *J. of Microwave Power*, vol. 14, No. 3, pp. 275–280 (1979).

Goodman, et al., "Magnetic Field Stress Induces Expression of *HSP70*", *Cell Stress & Chaperones* 3(2):79–88 (1998).

Grundler W., "Resonant Microwave Effect on Locally Fixed Yeast Microcolonies" *Z. Naturforsch* 44c:863–866 (1989).

Kim et al., "Anti–Stress and Anti–Fatigue Effects of Fermented Rice Bran", *Biosci Biotechnol Biochem.*, 65(10):2294–6 (2001).

Lin H. et al., "A Magnetic Field–Responsive Domain in the Human HSP70 Promoter", *J Cell Biochem*, 75:170–176 (1999).

Machado Caetano et al., "Immunopharmacological Effects of *Sacchoramyces Boulardii* in Healthy Human Volunteers", *Int'l Immunology and Immunopharmacology*, 8(3):245–259 (1986).

Ortuno et al., "Oral Administration of Yeast, *Saccharomyces Cerevisiae*, Enhances the Cellular Innate Immune response of Gilthead Seabream (*Sparus aurata L.*)", *Vet Immunol Immunopathol*, 85(1–2):41–50 (2002).

Peret Filho et al., "Dose Effect of Oral Saccharomyces Boulardii Treatments on Morbidity and Mortality in Immunosuppressed Mice", *J Med Microbiol.*, 47(2):111–6 (1998).

Saha et al., "Microbial Manipulation of Rumen Fermentation Using *Saccharomyces Cerevisiae* as Probiotics", *Current Science (Bangalore)*, 77(5):696–697 (1999).

WHO World Health Organization; WebPages http:www.who.int/peh–emf/about/WhatisEMF/en/ and http:www.who.int/peh–emf/about/WhatisEMF/en/index3.html *retrieved Jun. 10, 2004.*

METHODS AND COMPOSITIONS FOR TREATING GASTROPARESIS

FIELD OF THE INVENTION

The invention relates to compositions that can ameliorate or prevent gastroparesis and are useful as dietary supplements (e.g., health drinks) or medication (e.g., pills). These compositions contain yeast cells obtainable by growth in electromagnetic fields with specific frequencies and field strengths.

BACKGROUND OF THE INVENTION

Gastroparesis is a common condition. The upper portion of a human stomach generates electrical waves that sweep across the antrum, causing the stomach to contract, to grind food and to empty food into the intestines. Gastroparesis occurs when the rate of the electrical waves slow and the stomach muscles contract less frequently. Common symptoms of gastroparesis include nausea, vomiting, a feeling of fullness after only a few bites of food, bloating, and excessive belching.

Gastroparesis is caused by either diseases of the stomach muscles or the nerves that control these muscles. It is commonly associated with diabetes mellitus, which damages the nerves controlling the stomach muscle. Other causes include nervous reflexes, imbalance of potassium, calcium or magnesium, certain medications and certain diseases. Scars and fibrous tissue from ulcers and tumors that block the outlet of the stomach can mimic gastroparesis.

Gastroparesis is diagnosed based on symptoms and physical examination. A gastric emptying study is the most common method to measure the emptying of food from the stomach. An Upper gastrointestinal endoscopy test is another common examination to exclude the possibility of an obstruction as the cause of the patient's symptoms. An antro-duodenal motility study measures the pressure that is generated by the contractions of the stomach and intestinal muscles. Another test is an electrogastrogram (EGG), which records the electrical signals that travel through the stomach muscles and control the muscles' contractions. The electrical signals normally precede each contraction. In most patients, the rhythm of the electrical signals is either irregular or there is no post-meal increase in electrical power. Although an EGG does not measure gastric emptying directly, it is an attractive test for suspected gastroparesis.

Currently available medications treat gastroparesis by stimulating the stomach to contract more normally. Metoclopramide is an effective medication that has side effects such as restlessness, fatigue, agitation and depression. Another drug is domperidone, which has not been approved in the United States. The third drug is erythromycin, which stimulates short bursts of strong contractions that are more like the contractions that sweep undigested food into the colon than regular digestive contractions. Like erythromycin, octreotide, a hormone-like drug, can be injected underneath the skin to stimulate short bursts of strong contraction. The last resort is surgery, which is occasionally used to create a larger opening between the stomach and the small intestine in order to facilitate the process of emptying the stomach.

Gastroparesis may become worse with time. Motility disorders of the muscles of the small intestine and colon make gastroparesis difficult to treat. There remains a need for an effective treatment for gastroparesis.

SUMMARY OF THE INVENTION

This invention is based on the discovery that certain yeast cells can be activated by electromagnetic fields having specific frequencies and field strengths to produce substances useful in treating gastroparesis. Compositions comprising these activated yeast cells can therefore be used as medication, or dietary supplements in the form of health drinks or dietary pills (tablets or powder). For instance, these compositions can be used to alleviate gastroparesis symptoms in a human patient, or to prevent or postpone the onset of gastroparesis in a high risk individual (e.g., someone predisposed to gastroparesis because of his health or life style).

This invention embraces a composition comprising a plurality of yeast cells that have been cultured in an alternating electric field having a frequency in the range of about 9500 to 13500 MHz (e.g., 9500–10500, 11700–12700 and 12200–13200 MHz) and a field strength in the range of about 200–450 mV/cm (e.g., 235–255, 240–260, 250–270, 255–275, 265–285, 275–295, 280–300, 290–310, 290–320, 330–350 and 360–380 mV/cm). The yeast cells are cultured for a period of time sufficient to activate said plurality of yeast cells to produce substances useful in treating gastroparesis in a subject. In one embodiment, the frequency and/or the field strength of the alternating electric field can be altered within the aforementioned ranges during said period of time. In other words, the yeast cells are exposed to a series of electromagnetic fields. An exemplary period of time is about 10–50 hours.

Also included in this invention is a composition comprising a plurality of yeast cells that have been cultured under acidic conditions in an alternating electric field having a frequency in the range of about 10010–12800 MHz (e.g., 12600–12780 MHz) and a field strength in the range of about 235 to 380 mV/cm (e.g., 280–330 mV/cm). In one embodiment, the yeast cells are exposed to a series of electromagnetic fields. An exemplary period of time is about 10–100 hours.

Yeast cells that can be included in this composition can be derived from parent strains available from the China General Microbiological Culture Collection Center ("CGMCC"), China Committee for Culture Collection of Microorganisms, Institute of Microbiology, Chinese Academy of Sciences, Haidian, P.O. Box 2714, Beijing, 100080, China. Useful yeast species include, but are not limited to, those commonly used in food and pharmaceutical industries, such as *Saccharomyces* sp., *Schizosaccharomyces pombe, Saccharomyces sake, Saccharomyces uvarum, Saccharomyces rouxii, Saccharomyces cerevisiae, Saccharomyces carlsbergensis, Rhodotorula aurantiaca* and *Rhodotorula rubar*. For instance, the yeast cells can be of the strain *Saccharomyces cerevisiae* Hansen AS2.559, *Saccharomyces* sp. AS2.311, *Schizosaccharomyces pombe* Lindner AS2.994, *Saccharomyces sake* Yabe ACCC2045, *Saccharomyces uvarum* Beijer IFFI1044, *Saccharomyces rouxii* Boutroux AS2.180, *Saccharomyces cerevisiae* Hansen Var. *ellipsoideus* AS2.612, *Saccharomyces carlsbergensis* Hansen AS2.377, *Rhodotorula rubar* (Demme) Lodder AS2.282 and *Saccharomyces cerevisiae* Hansen AS2.69. Other useful yeast strains are illustrated in Table 1.

This invention further embraces a composition comprising a plurality of yeast cells, wherein said plurality of yeast cells have been activated to treat gastroparesis in a subject. Included in this invention are also methods of making these compositions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers. A subject includes a human and veterinary subject.

Other features and advantages of the invention will be apparent from the following detailed description, and from the claims.

DETAILED DESCRIPTION OF THE INVENTION

Figure 1:
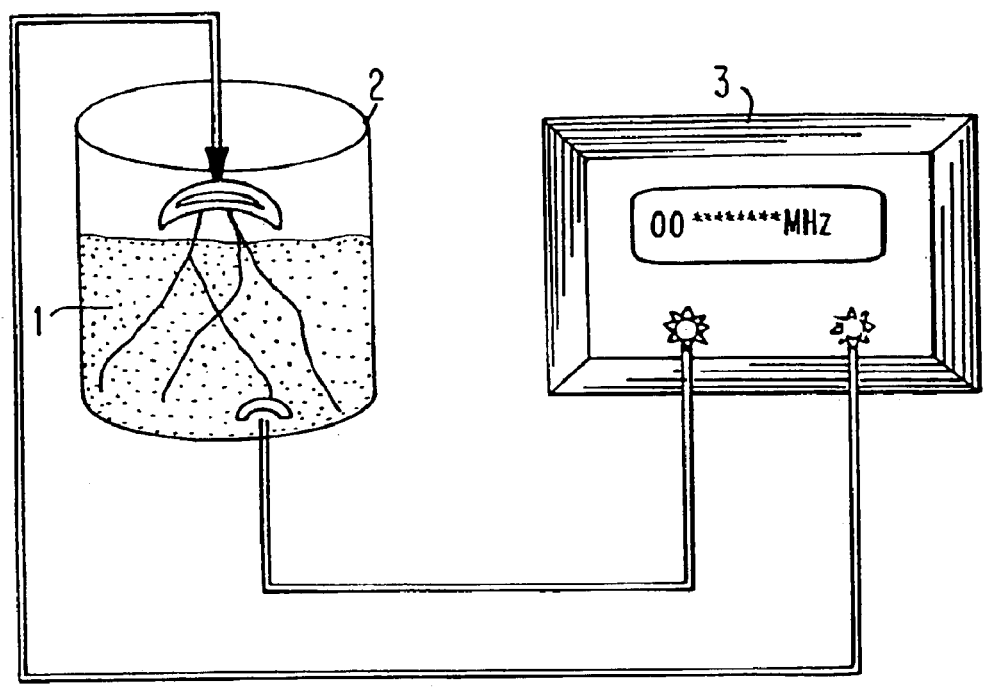
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to become highly efficient in producing substances that increase the bioelectrical activities of the stomach, reduce abnormal gastric acid secretion and/or abnormal pepsin production in a subject. Compositions containing these activated yeast cells are therefore useful in the treatment of gastroparesis. Yeast compositions containing activated yeast cells can be used as medication or dietary supplements.

Since the activated yeast cells contained in the yeast compositions have been cultured to endure acidic conditions (pH 2.5–4.2), these cells can survive the gastric environment and pass on to the intestines. Once in the intestines, the yeast cells are ruptured by various digestive enzymes, and the anti-gastroparesis substances are released and readily absorbed.

I. Yeast Strains Useful in the Invention

The types of yeasts useful in this invention include, but are not limited to, yeasts of the genera *Saccharomyces, Schizosaccharomyces*, and *Rhodotorula*.

Exemplary species within the above-listed genera include, but are not limited to, those illustrated in Table 1. Yeast strains useful for this invention can be obtained from laboratory cultures, or from publically accessible culture depositories, such as CGMCC and the American Type Culture Collection, 10801 University Boulevard, Manassas, Va. 20110–2209. Non-limiting examples of useful strains (with accession numbers of CGMCC) are *Saccharomyces cerevisiae* Hansen AS2.559 *Saccharomyces* sp. AS2.311, *Schizosaccharomyces pombe* Lindner AS2.994, *Saccharomyces sake* Yabe ACCC2045, *Saccharomyces uvarum* Beijer IFFI1044, *Saccharomyces rouxii* Boutroux AS2.180, *Saccharomyces cerevisiae* Hansen Var. *ellipsoideus* AS2.612, *Saccharomyces carlsbergensis* Hansen AS2.377, *Rhodotorula rubar* (*Demme*) Lodder AS2.282 and *Saccharomyces cerevisiae* Hansen AS2.69. Other useful yeast strains are illustrated in Table 1.

Although it is preferred, the preparation of the yeast compositions of this invention is not limited to starting with a pure strain of yeast. A yeast composition of the invention may be produced by culturing a mixture of yeast cells of different species or strains. The ability of any activated species or strain of yeasts to treat gastroparesis can be readily tested by methods known in the art. See, for instance, Examples 1 and 2.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| AS2.131 | AS2.213 |
|---|---|

*Saccharomyces delbrueckii*

| AS2.285 | |
|---|---|

*Saccharomyces delbrueckii* Lindner ver. mongolicus (Saito) Lodder et van Rij

| AS2.209 | AS2.1157 |
|---|---|

*Saccharomyces exiguous* Hansen

| AS2.349 | AS2.1158 |
|---|---|

*Saccharomyces fermentati* (Saito) Lodder et van Rij

| AS2.286 | AS2.343 |
|---|---|

*Saccharomyces logos* van laer et Denamur ex Jorgensen

| AS2.156 | AS2.327 | AS2.335 |
|---|---|---|

TABLE 1-continued

Exemplary Yeast Strains

*Saccharomyces mellis* (Fabian et Quinet) Lodder et kreger van Rij

AS2.195

*Saccharomyces mellis* Microellipsoides Osteralder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

| | | | |
|---|---|---|---|
| AS2.178 | AS2.180 | AS2.370 | AS2.371 |

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| | | | | |
|---|---|---|---|---|
| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. intermedia Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| | | | | |
|---|---|---|---|---|
| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| | | | | |
|---|---|---|---|---|
| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| | | |
|---|---|---|
| AS2.120 | AS2.281 | AS2.1180 |

*Crebrothecium ashbyii* (Guilliermond)
Routein (*Eremothecium ashbyii* Guilliermond)

| | | |
|---|---|---|
| AS2.481 | AS2.482 | AS2.1197 |

*Geotrichum candidum* Link

| | | | | |
|---|---|---|---|---|
| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| | | | | |
|---|---|---|---|---|
| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

TABLE 1-continued

Exemplary Yeast Strains

*Hansenula schneggii* (Weber) Dekker

AS2.304

*Hansenula subpelliculosa* Bedford

| | | | | |
|---|---|---|---|---|
| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| | | | | |
|---|---|---|---|---|
| ACCC2022 | ACCC2023 | AS2.197 | AS2.496 | AS2.714 |
| ACCC2021 | AS2.711 | | | |

*Lipomycess starkeyi* Lodder et van Rij

| | |
|---|---|
| AS2.1390 | ACCC2024 |

*Pichia farinosa* (Lindner) Hansen

| | | | | |
|---|---|---|---|---|
| ACCC2025 | ACCC2026 | AS2.86 | AS2.87 | AS2.705 |
| AS2.803 | | | | |

*Pichia membranaefaciens* Hansen

| | | | |
|---|---|---|---|
| ACCC2027 | AS2.89 | AS2.661 | AS2.1039 |

*Rhodosporidium toruloides* Banno

ACCC2028

*Rhodotorula glutinis* (Fresenius) Harrison

| | | | | |
|---|---|---|---|---|
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| | | | | |
|---|---|---|---|---|
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| | | | | |
|---|---|---|---|---|
| AS2.102 | AS2.107 | AS2.278 | AS2.499 | AS2.694 |
| AS2.703 | AS2.1146 | | | |

*Saccharomyces carlsbergensis* Hansen

| | | | | |
|---|---|---|---|---|
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| | | | | |
|---|---|---|---|---|
| IFFI1023 | IFFI1032 | IFFI1036 | IFFI1044 | IFFI1072 |
| IFFI1205 | IFFI1207 | | | |

*Saccharomyces willianus* Saccardo

| | | | | |
|---|---|---|---|---|
| AS2.5 | AS2.7 | AS2.119 | AS2.152 | AS2.293 |
| AS2.381 | AS2.392 | AS2.434 | AS2.614 | AS2.1189 |

*Saccharomyces* sp.

AS2.311

*Saccharomycodes ludwigii* Hansen

| | | |
|---|---|---|
| ACCC2044 | AS2.243 | AS2.508 |

*Saccharomycodes sinenses* Yue

AS2.1395

*Schizosaccharomyces octosporus* Beijerinck

| | |
|---|---|
| ACCC2046 | AS2.1148 |

*Schizosaccharomyces pombe* Lindner

| | | | | |
|---|---|---|---|---|
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

TABLE 1-continued

Exemplary Yeast Strains

*Sporobolomyces roseus* Kluyver et van Niel

| ACCC2049 | ACCC2050 | AS2.19 | AS2.962 | AS2.1036 |
|---|---|---|---|---|
| ACCC2051 | AS2.261 | AS2.262 | | |

*Torulopsis candida* (Saito) Lodder

| AS2.270 | ACCC2052 |
|---|---|

*Torulopsis famta* (Harrison) Lodder et van Rij

| ACCC2053 | AS2.685 |
|---|---|

*Torulopsis globosa* (Olson et Hammer) Lodder et van Rij

| ACCC2054 | AS2.202 |
|---|---|

*Torulopsis inconspicua* Lodder et Kreger van Rij

AS2.75

*Trichosporon behrendii* Lodder et Kreger van Rij

| ACCC2056 | AS2.1193 |
|---|---|

*Trichosporon capitatum* Diddens et Lodder

| ACCC2056 | AS2.1385 |
|---|---|

*Trichosporon cutaneum* (de Beurm et al.) Ota

| ACCC2057 | AS2.25 | AS2.570 | AS2.571 | AS2.1374 |
|---|---|---|---|---|

*Wickerhamia fluorescens* (Soneda) Soneda

| ACCC2058 | AS2.1388 |
|---|---|

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 9500 to 13500 MHz (e.g., 9500–10500, 11700–12700 and 12200–13200 MHz). Exemplary frequencies are 10012, 10038, 12177, 12712 and 12733 MHz. The field strength of the electric field useful in this invention ranges from about 200–450 mV/cm (e.g., 235–255, 240–260, 250–270, 255–275, 265–285, 275–295, 280–300, 290–310, 290–320, 330–350 and 360–380 mV/cm). Exemplary field strengths are 253, 255, 260, 277, 279, 280, 290, 293, 294, 314, 343 and 364 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of, for example, 2, 3, 4, 5, 6, 7, 8, 9, 10, 11, 12, 13 or more EMFs in a series. In one embodiment, the yeast culture is exposed to a series of EMFs, wherein the frequency of the electric field is alternated in the range of 9500–10500, 11700–12700 and 12200–13200 MHz.

Although the yeast cells can be activated after even a few hours of culturing in the presence of an EMF, it may be preferred that the activated yeast cells be allowed to multiply and grow in the presence of the EMF(s) for a total of 10–50 hours.

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 20,000 MHz. Signal generators capable of generating signals with a narrower frequency range can also be used. If desirable, a signal amplifier can also be used to increase the output. The activation container (2) can be made from non-conductive material, e.g., plastics, glass or ceramic. The wire connecting the activation container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of electrode wires used depends on the volume of the culture as well as the diameter of the wires. The number of metal wires/tubes used can be from 1 to 10 (e.g., 2 to 3). It is recommended, though not mandated, that for a culture having a volume up to 10 L, metal wires/tubes having a diameter of 0.5 to 2.0 mm be used. For a culture having a volume between 10 L and 100 L, metal wires/tubes having a diameter of 3.0 to 5.0 mm can be used. For a culture having a volume in the range of 100–1000 L, metal wires/tubes having a diameter of 6.0 to 15.0 mm can be used. For a culture having a volume greater than 1000 L, metal wires/tubes having a diameter of 20.0 to 25.0 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients assimilable by yeast cells. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 10% by weight of the medium and preferably between about 0.1% and 5% (e.g., about 2%). These carbon sources can be used individually or in combination. Amino acid-containing substances in suitable form (e.g., beef extract and peptone) can also be added individually or in combination. In general, the amount of amino acid containing substances varies between about 0.1% and 0.5% by weight of the medium and preferably between about 0.1% and 0.3% (e.g., about 0.25%). Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, $NaCl$, and $CaSO_4$.

IV. Electromagnetic Activation of Yeast Cells

To activate or enhance the ability of yeast cells to produce substances beneficial for the treatment of gastroparesis (e.g., stimulating stomach contraction), these cells can be activated by being cultured in an appropriate medium under sterile conditions at 20° C.–38° C., preferably at 28–32° C. (e.g., 30° C.) for a sufficient amount of time, e.g., 10–50 hours, in an alternating electric field or a series of alternating electric fields as described above.

An exemplary culture medium is made by mixing 1000 ml of distilled water with 18 g of mannitol, 20 μg of vitamin $B_{12}$, 40 μg of vitamin $B_6$, 10 μg of vitamin D, 35 ml of fetal bovine serum, 0.20 g of $KH_2PO_4$, 0.25 g of $MgSO_4.7H_2O$, 0.3 g of NaCl, 0.2 g of $CaSO_4.2H_2O$, 4.0 g of $CaCO_3.5H_2O$, and 2.5 g of peptone.

An exemplary set-up of the culturing process is depicted in FIG. 1. Untreated yeast cells are added to a culture medium at $1\times10^8$ cells per 1000 ml of the culture medium. The yeast cells may be *Saccharomyces cerevisiae* Hansen AS2.559, or may be selected from any of the strains listed in Table 1. An exemplary activation process of the yeast cells involves the following sequence: the yeast cells are grown in the culture medium for 23–43 hours (e.g., 28 hours) at 28–32° C. and then exposed to (1) an alternating electric field having a frequency of 10012 MHz and a field strength in the range of 240–260 mV/cm (e.g., 255 mV/cm) for 7–17 hours (e.g., 12 hours); (2) then to an alternating electric field having a frequency of 10038 MHz and a field strength in the range of 235–255 mV/cm (e.g., 253 mV/cm) for 31–41 hours (e.g., 36 hours); (3) then to an alternating electric field having a frequency of 12177 MHz and a field strength in the range of 265–285 mV/cm (e.g., 277 mV/cm) for 36–46 hours (e.g., 41 hours); (4) then to an alternating electric field having a frequency of 12712 MHz and a field strength in the range of 290–310 mV/cm (e.g., 294 mV/cm) for 20–30 hours (e.g., 25 hours); and (5) finally to an alternating electric field having a frequency of 12733 MHz and a field strength in the range of 255–275 mV/cm (e.g., 260 mV/cm) for 10–20 hours (e.g., 15 hours). The activated yeast cells are then recovered from the culture medium by various methods known in the art, dried (e.g., by lyophilization) and stored at about 4° C. in powder form. The resultant yeast powder preferably contains no less than $10^{10}$ cells/g activated yeast.

Subsequently, the activated yeast cells can be evaluated for their ability to treat gastroparesis using standard methods known in the art, such as those described in Section VII.

V. Acclimatization of Yeast Cells to the Gastric Environment

Because the activated yeast cells of this invention must pass through the stomach before reaching the small intestine, where the effective components are released from these yeast cells, it is preferred that these yeasts be cultured under acidic conditions so as to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture can then be cultured first in the presence of an alternating electric field having a frequency of 12712 MHz and a field strength in the range of 290–320 mV/cm (e.g., 314 mV/cm) at about 28 to 32° C. for 36–42 hours (e.g., 38 hours). The resultant yeast cells can then be further incubated in the presence of an alternating electric field having a frequency of 12733 MHz and a field strength in the range of 275–295 mV/cm (e.g., 290 mV/cm) at about 28 to 32° C. for 16–28 hours (e.g., 20 hours). The resulting acclimatized yeast cells are then recovered from the culture medium by various methods known in the art and are dried and stored either in powder form ($\geq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of acclimatizing culture medium is adjusted to 2.5 with 0.1 M hydrochloric acid (HCl) and 0.2 M potassium hydrogen phthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
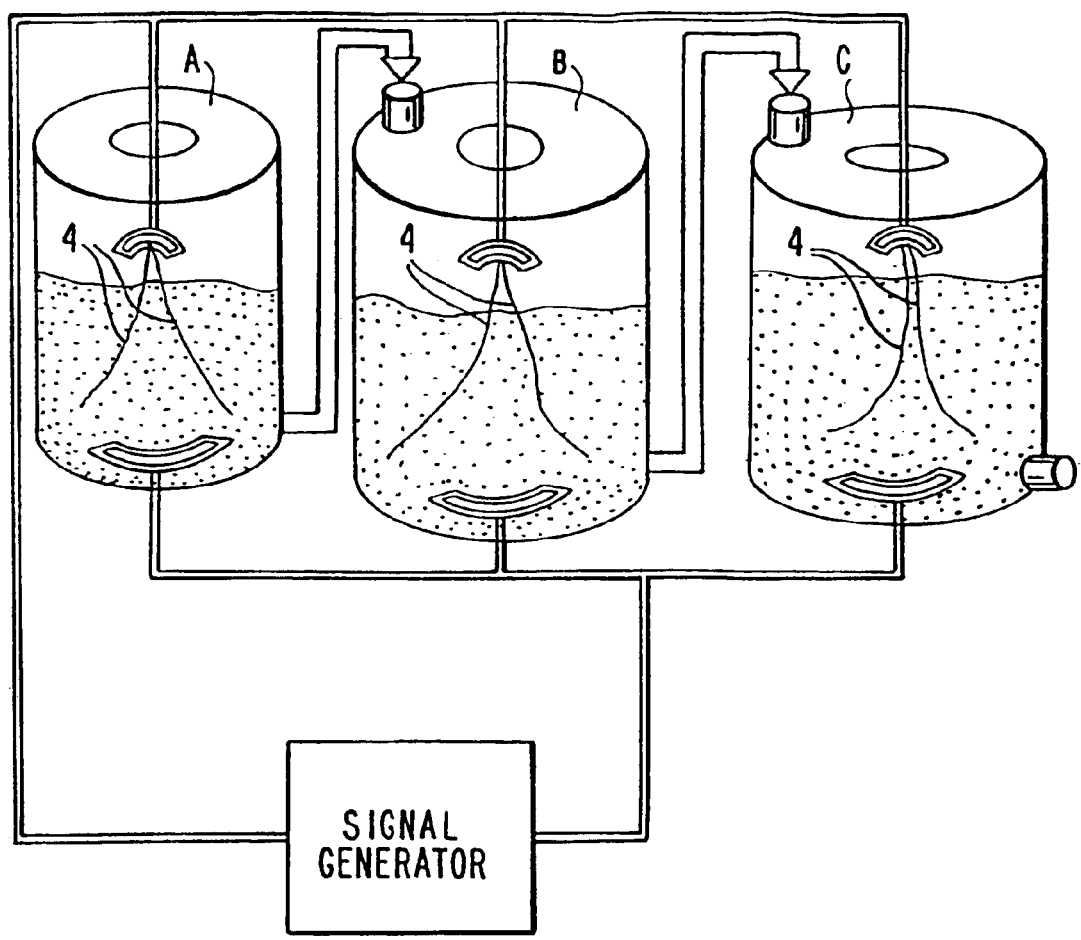
FIG. 2 is a schematic diagram showing an exemplary apparatus for making yeast compositions of the invention. The apparatus comprises a signal generator and interconnected containers A, B and C.

To prepare the yeast compositions of the invention, an apparatus depicted in FIG. 2 or an equivalent thereof can be used. This apparatus includes three containers, a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of *Schisandra chinensis* (*Turez*) *Baill* seeds extract, and 100 L of soy bean extract. To prepare hawthorn, jujube and *Schisandra chinensis* (*Turez*) *Baill* seeds extracts, the fresh fruits are washed and dried under sterile conditions to reduce the water content to no higher than 8%. One hundred kilograms of the dried fruits are then ground ($\geq 20$ mesh) and added to 400 L of sterilized water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterilized water. The mixture is stirred under sterile conditions at room temperature for twelve hours and centrifuged at 1000 rpm to remove insoluble residues. Once the mixed fruit extract solution is prepared, it is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (A) shown in FIG. 2. The yeast cells are then cultured in the presence of an alternating electric field having a frequency of 12712 MHz and a field strength of about 360–380 mV/cm (e.g., 364 mV/cm) at 28–32° C. under sterile conditions for 19–29 hours (e.g., 24 hours). The yeast cells are further incubated in an alternating electric field having a frequency of 12733 MHz and a field strength of 280–300 mV/cm (e.g., 293 mV/cm). The culturing continues for 7–17 hours (e.g., 12 hours).

The yeast culture is then transferred from the first container (A) to the second container (B) (if need be, a new batch of yeast culture can be started in the now available the first container (A)), and subjected to an alternating electric field having a frequency of 12712 MHz and a field strength of 265–285 mV/cm (e.g., 279 mV/cm) for 19–29 hours (e.g., 24 hours). Subsequently the frequency and field strength of the electric field are changed to 12733 MHz and 250–270 mV/cm (e.g., 260 mV/cm), respectively. The culturing process continues for 7–17 hours (e.g., 12 hours).

The yeast culture is then transferred from the second container (B) to the third container (C), and subjected to an alternating electric field having a frequency of 12712 MHz and a field strength of 265–285 mV/cm (e.g., 279 mV/cm) for 19–29 hours (e.g., 24 hours). Subsequently the frequency and field strength of the electric field are changed to 12733 MHz and 250–270 mV/cm (e.g., 260 mV/cm), respectively. The culturing continues for 7–17 hours (e.g., 12 hours).

The yeast culture from the third container (C) can then be packaged into vacuum sealed bottles for use as dietary supplement or medication. The compositions may be conveniently formulated as health drinks. If desired, the final yeast culture can also be dried within 24 hours and stored in powder form. The dietary supplement or medication can be taken three to four times daily at 30–50 ml or 100 ml per bottle for a three-month period (preferably a six-month period), preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound ($\geq 18000$ Hz) for 10 minutes and then centrifuged at 4355 rpm for another 10 minutes. The resulting supernatant is adjusted to pH 7.2–7.4 using 1 M NaOH and subsequently filtered through a membrane (0.22 µm for intravenous injection and 0.45 µm for peritoneal injection) under sterile conditions. The resulting sterile preparation is submerged in a 35–38° C. water bath for 30 minutes before use. In other embodiments, the compositions of the invention may also be formulated with pharmaceutically acceptable carriers to be orally administered in any orally acceptable dosage form including, but not limited to, capsules, tablets, suspensions or solutions.

The yeast compositions of the present invention are derived from yeasts used in food and pharmaceutical industries. The yeast compositions are thus devoid of side effects associated with many pharmaceutical compounds.

VII. Examples

In order that this invention be more fully understood, the following examples are set forth. These examples are for the purpose of illustration only and are not to be construed as limiting the scope of the invention in any way.

The activated yeast compositions used in the following examples were prepared as described above, using *Saccharomyces cerevisiae* Hansen AS2.559, cultured in the presence of an alternating electric field having the electric field frequency and field strength exemplified in the parentheses following the recommended ranges listed in Section IV, supra. Control (i.e., untreated) yeast compositions were those prepared in the same manner as described in Section IV, supra, except that the yeast cells were cultured in the absence of EMFs. Unless otherwise specified, all compositions of interest were administered to the animals by intragastric feeding.

EXAMPLE 1

Effects of Yeast Compositions on Stomach Contraction

To test the ability of the activated yeast compositions to stimulate stomach contraction, thirty domestic rabbits (*Oryctolagus curiculus*) of average weight of about 2.0±0.2 kg (3–5 months old, half of them male and the other half female) were fasted for 16 hours and subsequently randomly divided into three groups, designated as AY, NY and CK.

Each rabbit was anesthetized by injection of 0.8 ml of a 2.5 g/dl pentobarbital solution through its marginal ear vein. A No. 10 urinary catheter was inserted into the stomach of the rabbit through its mouth (about 22 cm from its teeth) for feeding. See, e.g., Zhu Yu et al., Eds., Animal Disease Models, Tian Jin Science and Technology Translation Publishing Company (1997).

Each rabbit was then placed in a supine position on a rabbit board. The fur around the xiphoid process or ensistemum was shaved and the exposed skin was rubbed with 95% alcohol to remove surface oil. An electrode was placed onto the rabbit's abdomen over the gastric antrum, which was about 1 cm below and 1 cm to the left of xiphoid process. Another electrode was placed over the stomach, which was about 1 cm below and 1 cm to the right of xiphoid process. An electrogastrogram (EGG) was taken for 5 to 10 minutes first over gastric antrum and then over the stomach before the rabbits were fed.

Rabbits in the AY group were each given 2 ml of the activated yeast composition. Rabbits in the NY group were each given 2 ml of the control yeast composition. Rabbits in the CK group were each given 2 ml of saline. The rabbits in all three groups were otherwise maintained under the same conditions. An EGG was taken for each rabbit, first over the gastric antrum and then over the stomach, at 30 minutes and 60 minutes after feeding.

Figure 3:
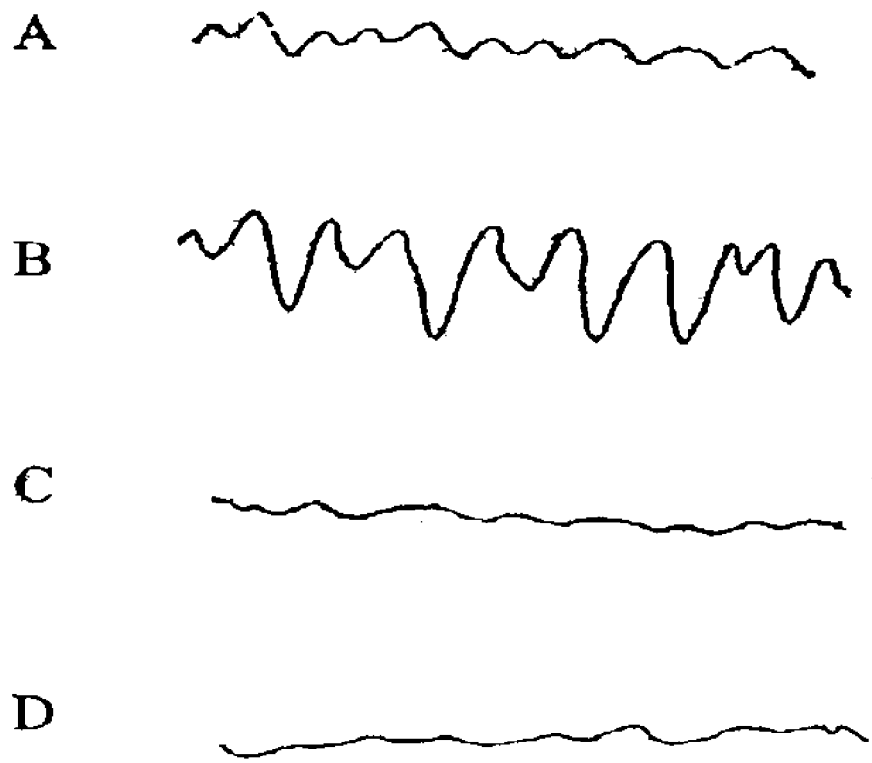
FIG. 3 shows representative EGGs. A represents an electrogastrogram of rabbits before feeding; B represents an electrogastrogram of rabbits in the AY group at 60 minutes after feeding; C represents an electrogastrogram of rabbits in the NY group at 60 minutes after feeding; and D represents an electrogastrogram of rabbits in the CK group at 60 minutes after feeding.

A representative EGG before and after feeding for rabbits in each group is shown in FIG. 3. The average frequency (1/min.) and intensity (µV) of electrical signals recorded on EGGs over a period of 3 to 5 minutes are summarized in Table 2a and Table 2b, respectively.

TABLE 2a

Effects of Treatment on the Frequency of Electrical Signals

| Time | Gastric Antrum | | | Stomach | | |
|---|---|---|---|---|---|---|
| (min.) | AY | NY | CK | AY | NY | CK |
| 0 | 2.7 ± 0.6 | 2.8 ± 0.5 | 2.8 ± 0.6 | 2.1 ± 0.5 | 2.3 ± 0.6 | 2.4 ± 0.5 |
| 30 | 2.6 ± 0.7 | 2.7 ± 0.5 | 2.7 ± 0.8 | 2.4 ± 0.5 | 1.8 ± 0.6 | 1.9 ± 0.7 |
| 60 | 2.9 ± 0.2 | 2.7 ± 0.7 | 2.7 ± 0.6 | 2.1 ± 0.4 | 2.7 ± 0.5 | 2.7 ± 0.7 |

TABLE 2b

Effects of Treatment on the Intensity of Electrical Signals

| Time | Gastric Antrum | | | Stomach | | |
|---|---|---|---|---|---|---|
| (min.) | AY | NY | CK | AY | NY | CK |
| 0 | 112 ± 67.6 | 107 ± 59.8 | 115 ± 71.2 | 29.3 ± 9.7 | 23.7 ± 10.6 | 25.8 ± 11.3 |
| 30 | 242 ± 37.6 | 122 ± 32.5 | 127 ± 33.8 | 52.5 ± 22.6 | 31.1 ± 1.1 | 30.2 ± 0.8 |
| 60 | 157 ± 17.3 | 121 ± 39.6 | 125 ± 41.8 | 58.4 ± 10.6 | 24.6 ± 0.7 | 25.4 ± 0.5 |

The above results show that unlike the control yeast composition or saline, the activated yeast composition could stimulate the stomach to contract by increasing the intensity of the electrical signals over both the gastric antrum and the stomach.

EXAMPLE 2

Effects of the Treatment on Gastric Acid and Pepsin

Thirty Wistar rats of average weight of about 180–200 g (4–6 months old) were randomly divided into three equal groups. Rats in the AY group were administered 2 ml of the activated yeast composition once daily for five days. Rats in the NY and CK groups were given 2 ml of the control yeast composition and saline once daily for five days, respectively. The rats in all three groups were otherwise maintained under the same conditions.

After the fifth dose of yeast composition was administered to the animals, the animals were given only water, but no food, for the next 24 hours. The rats were then anesthetized with ether. An incision was then made in the middle of the abdomen of the animal and the stomach was located. The pylorus was then ligated. The activated yeast composition, control yeast composition, and saline were administered at 3 ml/kg body weight through the duodenum by injection to rats in the AY, NY and CK groups, respectively. Then, the incision was stitched. Two hours later, the animals were sacrificed. The whole stomach was removed. The gastric contents were emptied into a conical centrifuge tube, measured for its volume and pH value, and centrifuged at 1500 rpm for 10 minutes. The supernatant was collected.

The pepsin concentration in the gastric juice was determined by the HPLC method.

The experimental results are summarized in Table 3 below.

TABLE 3

Effects of Treatment on Secretion of Gastric Acid and Pepsin Activity

| Group | Gastric Juice (ml) | Gastric Acid ($\mu$M) | Pepsin Activity ($\mu$M) |
|---|---|---|---|
| CK | 11.2 ± 2.1 | 1.2 ± 0.5 | 92.2 ± 23.3 |
| NY | 10.7 ± 2.2 | 1.1 ± 0.4 | 91.7 ± 22.4 |
| AY | 4.8 ± 1.8 | 0.4 ± 0.2 | 43.6 ± 13.6 |

These data demonstrate that the activated yeast composition decreased gastric acid concentration and pepsin activity, as compared to the control yeast composition and saline.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to treat gastroparesis in a subject, as a result of having been cultured in the presence of an alternating electric field having a frequency in the range of 9500 to 13500 MHz and a field strength in the range of 200 to 450 mV/cm, as compared to yeast cells not having been so cultured.

2. The composition of claim 1, wherein said frequency is in the range of 9500–10500, 11700–12700 or 12200–13200 MHz.

3. The composition of claim 1, wherein said field strength is in the range of 235–255, 240–260, 250–270, 255–275, 265–285, 275–295, 280–300, 290–310, 290–320, 330–350 or 360–380 mV/cm.

4. The composition of claim 1, wherein said yeast cells are cells of the species *Saccharomyces* sp., *Schizosaccharomyces pombe*, *Saccharomyces sake*, *Saccharomyces uvarum*, *Saccharomyces rouxii*, *Saccharomyces cerevisiae*, *Saccharomyces carlsbergensis*, *Rhodotorula aurantiaca* and *Rhodotorula rubar*.

5. The composition of claim 1, wherein said yeast cells are derived from cells of the strain deposited at the China General Microbiological Culture Collection Center with an accession number selected from the group consisting of AS2.559, AS2.311, AS2.994, ACCC2045, IFFI1044, AS2.180, AS2.612, AS2.377, AS2.282 and AS2.69.

6. The composition of claim 1, wherein said composition is in the form of a tablet, powder, or a health drink.

7. The composition of claim 6, wherein said composition is in the form of a health drink.

8. The composition of claim 1, wherein said gastroparesis is associated with diabetes.

9. A method of preparing a yeast composition, comprising culturing a plurality of yeast cells in the presence of an alternating electric field having a frequency in the range of 9500 to 13500 MHz and a field strength in the range of 200 to 450 mV/cm for a period of time sufficient to result in the capability of said composition to treat gastroparesis in a subject as compared to yeast cells not having been so cultured.

10. A method according to claim 9, wherein said frequency is in the range of 9500–10500, 11700–12700 or 12200–13200 MHz.

11. A method for treating gastroparesis in a subject, comprising orally administering to said subject the composition of claim 1.

12. A method of claim 11 comprising oral administration.

* * * * *

UNITED STATES PATENT AND TRADEMARK OFFICE
CERTIFICATE OF CORRECTION

PATENT NO.     : 6,979,562 B2
DATED          : December 27, 2005
INVENTOR(S)    : Ling Yuk Cheung It is certified that error appears in the above-identified patent and that said Letters Patent is hereby corrected as shown below:

Column 12,
Lines 44-45, "ensistemum" should read -- ensisternum --.

Signed and Sealed this

Eleventh Day of April, 2006

JON W. DUDAS
*Director of the United States Patent and Trademark Office*